United States Patent
Twomey et al.

(10) Patent No.: US 9,486,220 B2
(45) Date of Patent: Nov. 8, 2016

(54) SURGICAL TISSUE OCCLUDING DEVICE

(75) Inventors: John R. Twomey, Longmont, CO (US);
James D. Allen, IV, Broomfield, CO (US); Kim V. Brandt, Loveland, CO (US); Keir Hart, Lafayette, CO (US); Daniel A. Joseph, Golden, CO (US); Duane E. Kerr, Loveland, CO (US); Peter M. Mueller, Frederick, CO (US); Jeffrey R. Unger, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 1412 days.

(21) Appl. No.: 13/247,778

(22) Filed: Sep. 28, 2011

(65) Prior Publication Data

US 2013/0079760 A1    Mar. 28, 2013

(51) Int. Cl.
*A61F 5/08* (2006.01)
*A61B 17/12* (2006.01)
*A61B 18/14* (2006.01)
*A61B 18/18* (2006.01)
*A61B 18/00* (2006.01)
*A61B 17/00* (2006.01)

(52) U.S. Cl.
CPC ..... *A61B 17/12013* (2013.01); *A61B 18/1445* (2013.01); *A61B 18/18* (2013.01); *A61B 2017/00831* (2013.01); *A61B 2017/00867* (2013.01); *A61B 2017/00955* (2013.01); *A61B 2018/00047* (2013.01)

(58) Field of Classification Search
CPC ....... A61B 18/24; A61B 18/22; A61B 18/20
USPC .............................................. 606/13–15, 151
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — William Thomson
*Assistant Examiner* — Jeffrey Lipitz

(57) ABSTRACT

A surgical instrument includes an end effector assembly having first and second jaw members moveable relative to one another between a spaced-apart position and an approximated position for grasping tissue therebetween. In the approximated position, the jaw members cooperate to define a cavity that is configured to house tissue grasped between the jaw members. An injectable material configured for injection into the cavity defined by the jaw members is also provided. The injectable material is configured to substantially surround tissue housed within the cavity. The injectable material is transitionable from a first state, facilitating injection of the injectable material into the cavity, to a second state, wherein the injectable material forms about tissue housed within the cavity to occlude tissue.

5 Claims, 7 Drawing Sheets

(56) References Cited

U.S. PATENT DOCUMENTS

| | | | |
|---|---|---|---|
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| 6,099,537 A | 8/2000 | Sugai et al. | |
| H1904 H * | 10/2000 | Yates | A61B 17/07207 606/142 |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,663,639 B1 | 12/2003 | Laufer et al. | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| 2003/0069571 A1 | 4/2003 | Treat et al. | |
| 2004/0073256 A1 | 4/2004 | Marchitto et al. | |
| 2004/0210282 A1 | 10/2004 | Flock et al. | |
| 2007/0074807 A1* | 4/2007 | Guerra | A61B 18/1445 156/242 |
| 2008/0114381 A1* | 5/2008 | Voegele | A61B 17/10 606/151 |
| 2008/0125797 A1 | 5/2008 | Kelleher | |
| 2008/0255476 A1* | 10/2008 | Boyajian | A61N 1/36007 600/593 |
| 2010/0049194 A1 | 2/2010 | Hart et al. | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.

(56) References Cited

OTHER PUBLICATIONS

U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.

(56) References Cited

OTHER PUBLICATIONS

Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.

(56) References Cited

OTHER PUBLICATIONS

Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/USO4/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

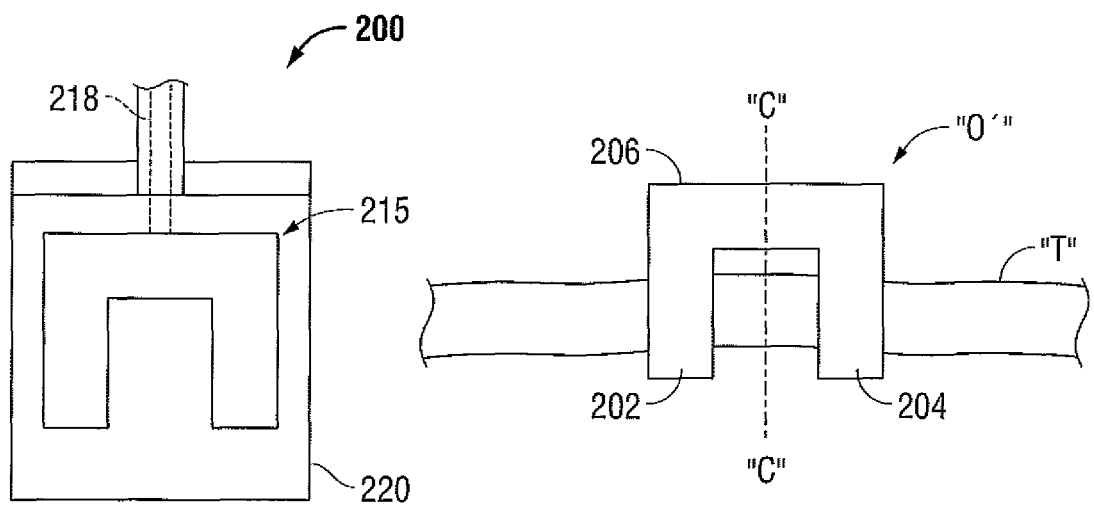
FIG. 7A  FIG. 7B
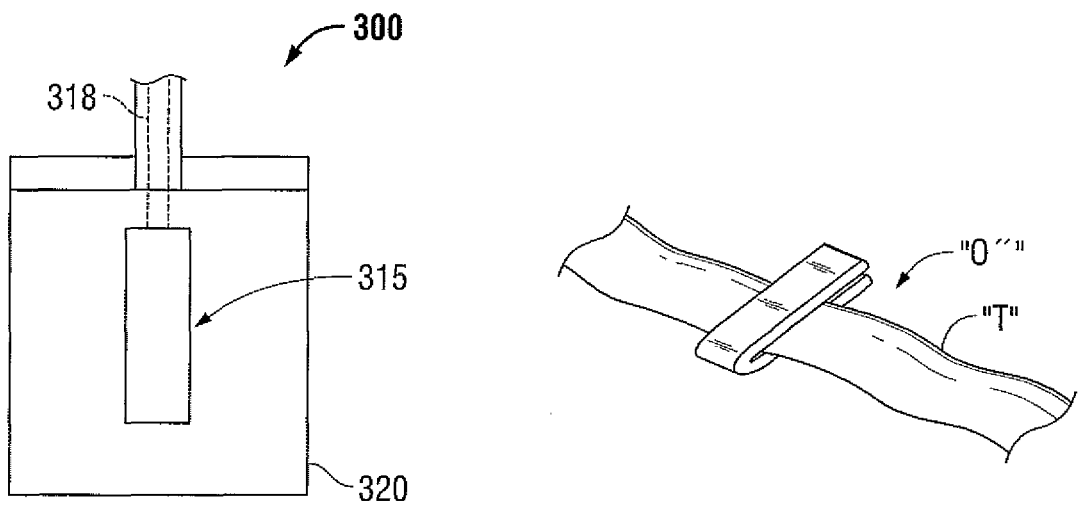
FIG. 8A  FIG. 8B

SURGICAL TISSUE OCCLUDING DEVICE

BACKGROUND

1. Technical Field

The present disclosure relates to surgical instruments and, more particularly, to a surgical instrument for grasping, occluding and/or dividing tissue.

2. Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue occlude.

SUMMARY

As used herein, the term "distal" refers to the portion that is being described which is further from a user, while the term "proximal" refers to the portion that is being described which is closer to a user. To the extent consistent with one another, any of the aspects described herein may be used in conjunction with any or all of the other aspects described herein.

In accordance with one aspect of the present disclosure, a surgical instrument is provided. The surgical instrument includes an end effector assembly having first and second jaw members moveable relative to one another between a spaced-apart position and an approximated position for grasping tissue therebetween. In the approximated position, the jaw members cooperate to define a cavity that is configured to house tissue grasped between the jaw members. An injectable material configured for injection into the cavity defined by the jaw members is also provided. The injectable material is configured to substantially surround tissue housed within the cavity and is transitionable from a first state, facilitating injection of the injectable material into the cavity, to a second state, wherein the injectable material forms about tissue housed within the cavity to occlude tissue.

In one aspect, the surgical instrument further includes a replaceable material reservoir cartridge configured to retain the injectable material therein.

In another aspect, the injectable material is transitionable from a fluid state, facilitating injection of the injectable material into the cavity, to a solid state, wherein the injectable material forms about tissue housed within the cavity to occlude tissue. The first, or fluid state of the injectable material may correspond to a heated state, while the second, or solid state of the injectable material may correspond to a cooled state.

In another aspect, a knife assembly is provided. The knife assembly includes a knife blade selectively translatable between the jaw members to divide the formed injectable material and occluded tissue.

In yet another aspect, the cavity formed by the jaw members in the approximated position defines a cylindrical configuration such that the formed injectable material defines a cylindrical member disposed about tissue.

In still another aspect, the cavity formed by the jaw members defines a U-shaped configuration such that the formed injectable material defines a U-shaped member disposed about tissue.

In still yet another aspect, the formed injectable material defines a clip-like member disposed about tissue.

In another aspect, the jaw members are configured to apply UV energy to the injectable material disposed within the cavity to transition the injectable material from the first state to the second state.

A tissue occlusion device is also provided in accordance with the present disclosure. The tissue occlusion device includes an elongated body bistable in both a first state, wherein the body defines a substantially straight configuration, and a second state, wherein the body defines a coiled configuration. The elongated body is positionable adjacent tissue and is transitionable from the first state to the second state to coil about tissue to occlude tissue.

In one aspect, the elongated body is transitioned from the first state toward the second state by breaking the substantially straight configuration of the elongated body.

In another aspect, the elongated body is formed at least partially from a bistable spring, the elongated body transitionable from the first state to the second state to coil about tissue under mechanical bias of the bistable spring to occlude tissue.

In yet another aspect, the elongated body is configured to be heat-shrunk about tissue to occlude tissue.

In still another aspect, the elongated body is configured to be UV-shrunk about tissue to occlude tissue.

In another aspect, the elongated body is formed at least partially from a shape-memory material that is configured to form about tissue to occlude tissue.

In still yet another aspect, the elongated body, in the coiled configuration, defines a plurality of windings, i.e., the elongated body is wound-up about itself multiple times in the coiled configuration.

A method of occluding tissue is also provided in accordance with the present disclosure. The method includes coagulating tissue, positioning a tissue occlusion device adjacent coagulated tissue, and transitioning the tissue occlusion device from a first state to a second state to coil about coagulated tissue to occlude coagulated tissue. Tissue may be coagulated by conducting UV energy therethrough. The tissue occlusion device may be configured similarly to any of the tissue occlusion devices above.

Provided in accordance with the present disclosure is another aspect of a method of occluding tissue. The method includes positioning tissue within a cavity defined within an end effector assembly of a surgical instrument, providing a material transitionable from a first state to a second state, injecting the material into the cavity defined within the end effector assembly such that the material surrounds tissue disposed within the cavity, and transitioning the material from the first state to the second state such that the injectable material forms about tissue disposed within the cavity to occlude tissue.

In one aspect, the step of transitioning the material from the first state to the second state includes transitioning the material from a liquid state to a solid state. Alternatively, the material may be transitioned from a gaseous state to a solid state, or from a gaseous state to a liquid state to a solid state.

In another aspect, the material is transitioned from the first state to the second state via cooling (or heating) of the material. Alternatively, the material may be transitioned from the first state to the second state via UV-curing.

In still another aspect, the method further includes cutting the formed injectable material to divide the occluded tissue.

In yet another aspect, the cavity defines a pre-determined configuration such that the formed injectable material defines a configuration complementary to that of the cavity.

BRIEF DESCRIPTION OF THE DRAWINGS

Various aspects of the present disclosure are described herein with reference to the drawings wherein like reference numerals identify similar or identical elements:

FIG. 7A is a top view of a jaw member of an end effector assembly configured for use with the surgical instrument of FIG. 1 or 2;

FIG. 7B is a top view of a portion of tissue occluded using an end effector assembly including the jaw member of FIG. 7A;

FIG. 8A is a top view of yet another jaw member of an end effector assembly configured for use with the surgical instrument of FIG. 1 or 2;

FIG. 8B is a top view of a portion of tissue occluded using an end effector assembly including the jaw member of FIG. 8A;

DETAILED DESCRIPTION

Figure 1:
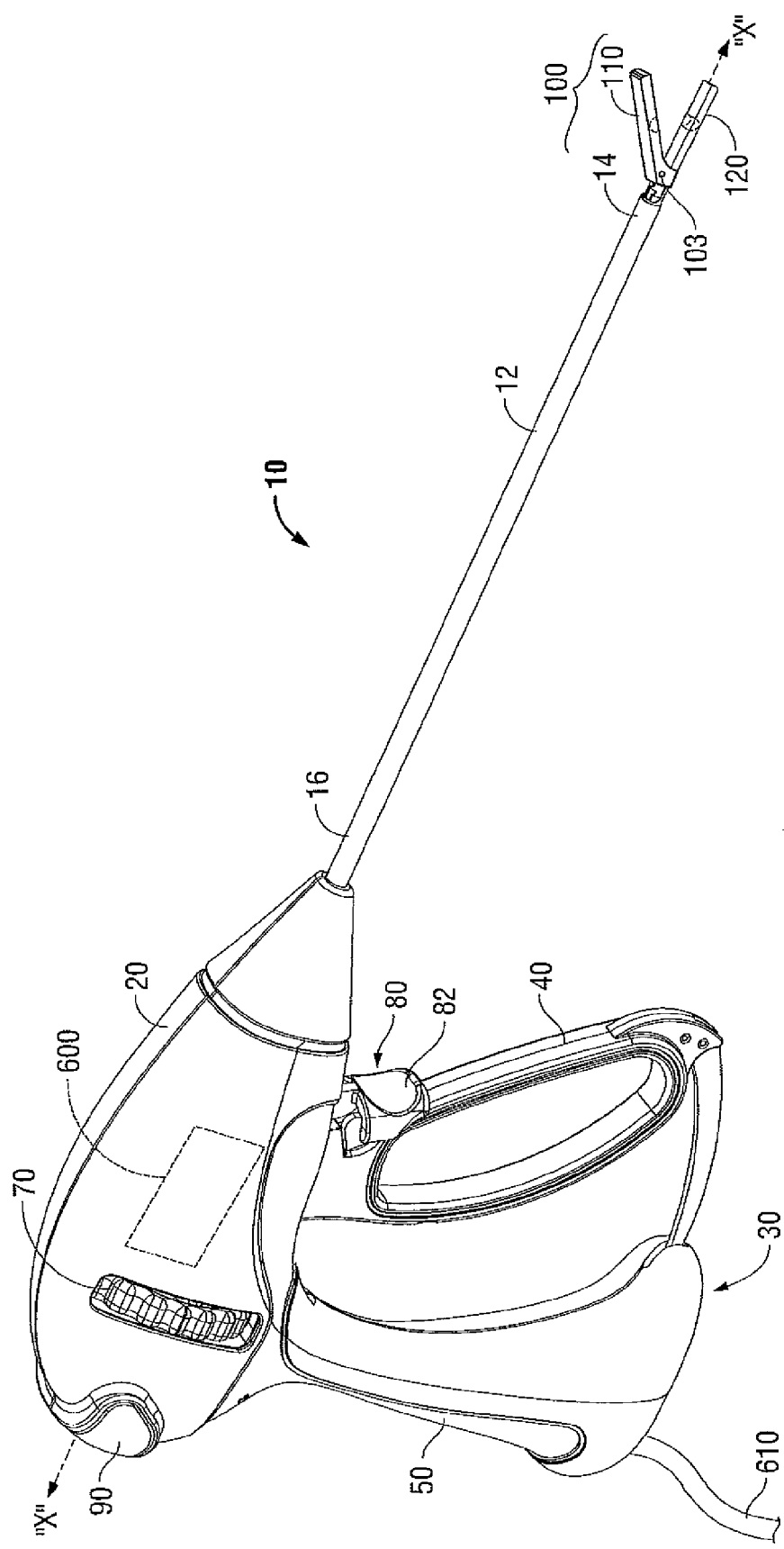
FIG. 1 is a front, perspective view of an endoscopic surgical instrument configured for use in accordance with the present disclosure.
Figure 2:
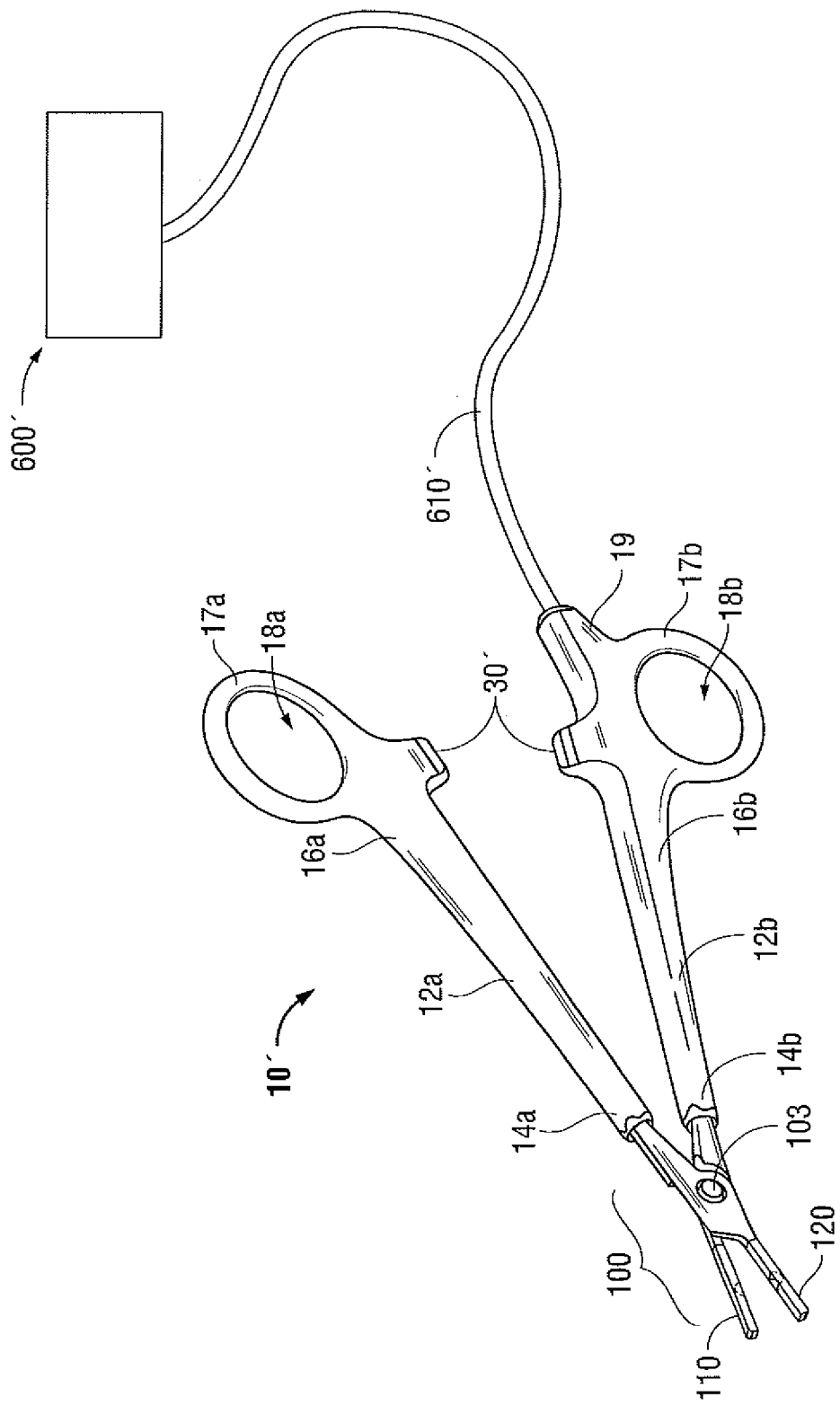
FIG. 2 is a front, perspective view of an open surgical instrument configured for use in accordance with the present disclosure.

Referring now to FIGS. 1 and 2, FIG. 1 depicts an instrument 10 for use in connection with endoscopic surgical procedures and FIG. 2 depicts an open instrument 10' contemplated for use in connection with traditional open surgical procedures. For the purposes herein, either an endoscopic instrument, e.g., instrument 10, or an open instrument, e.g., instrument 10', may be utilized in accordance with the present disclosure. Obviously, different considerations apply to each particular type of instrument, however, the novel aspects with respect to the end effector assembly and its operating characteristics remain generally consistent with respect to both the open and endoscopic configurations.

Turning now to FIG. 1, an endoscopic instrument 10 is provided defining a longitudinal axis "X-X" and including a housing 20, a handle assembly 30, a rotating assembly 70, a trigger assembly 80 and an end effector assembly 100. Instrument 10 further includes a shaft 12 having a distal end 14 configured to mechanically engage end effector assembly 100 and a proximal end 16 that mechanically engages housing 20. Instrument 10 also includes a cable 610 that connects instrument 10 to a power source (not shown) for heating the material disposed within material reservoir 600, although instrument 10 may alternatively be configured as a battery powered instrument.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about longitudinal axis "X-X" to rotate end effector 100 about longitudinal axis "X-X." Housing 20 houses the internal working components of instrument 10, including material reservoir 600. Material reservoir 600 is coupled to a supply lumen (not explicitly shown) that extends through shaft 12 such that the material disposed within material reservoir 600 may be selectively supplied to end effector assembly 100 through tubes 118, 128 (FIGS. 3A-3B), e.g., via actuation of activation switch 90, as will be described in greater detail hereinbelow. Further, material reservoir 600 may be removable or refillable for preparing surgical instrument 10 for reuse. In particular, material reservoir 600 may be configured as a replaceable cartridge that is removably engageable within housing 20 of forceps 10. Accordingly, material reservoir 600 may be replaced after each procedure with a new material reservoir 600 and/or the material reservoir 600 may be selected from various different material reservoirs 600 containing various different materials, depending on a particular purpose. Alternatively, surgical instrument 10 may be configured as a disposable instrument. In either configuration, material reservoir 600 is fillable with a biocompatible material, e.g., a plastic or epoxy, configured to transition between a fluid state (FIG. 5B), i.e., wherein the material is in a liquid or gaseous state, and a solid state (FIGS. 6A-6B), e.g., upon heating/cooling thereof. On the other hand, the material may be configured to transition from the fluid state to the solid state upon application of ultraviolet (UV) energy thereto, e.g., via UV-curing. Materials suitable for UV-curing include biocompatible polymers or any other suitable UV-curable materials.

End effector assembly 100 is shown attached at a distal end 14 of shaft 12 and includes a pair of opposing jaw members 110 and 120. End effector assembly 100 is designed as a unilateral assembly, i.e., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, i.e., where both jaw member 110 and jaw member 120 are moveable about a pivot 103 relative to one another and to shaft 12. In some embodiments, a knife assembly 180 (FIGS. 4A-4C) is disposed within shaft 12 that is configured to selectively reciprocate a knife blade 182 (FIG. 4A-4C) through jaw members 110, 120, e.g., via activation of a trigger 82 of trigger assembly 80. End effector assembly 100 will be described in greater detail hereinbelow.

Continuing with reference to FIG. 1, moveable handle 40 of handle assembly 30 is ultimately connected to a drive assembly (not shown) that, together, mechanically cooperate to impart movement of jaw members 110 and 120 between a spaced-apart position and an approximated position to grasp tissue therebetween. As shown in FIG. 1, moveable handle 40 is initially spaced-apart from fixed handle 50 and, correspondingly, jaw members 110, 120 are in the spaced-apart position. Moveable handle 40 is actuatable from this initial position to a depressed position corresponding to the approximated position of jaw members 110, 120 (see FIGS. 4B-4C).

Referring now to FIG. 2, an open instrument 10' is shown including two elongated shafts 12a and 12b, each having a proximal end 16a and 16b, and a distal end 14a and 14b, respectively. Similar to instrument 10 (FIG. 1), instrument 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably connected about a pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another which, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30' may be included for selectively locking the jaw members 110 and 120 relative to one another at various positions during pivoting. Ratchet 30' may include graduations or other visual markings that enable the user to easily and quickly ascertain and control the amount of closure force desired between the jaw members 110 and 120.

With continued reference to FIG. 2, one of the shafts, e.g., shaft 12b, includes a proximal shaft connector 19 that is designed to connect the instrument 10' to material reservoir 600'. Proximal shaft connector 19 secures a cable 610' to instrument 10' such that the user may selectively supply material from the material reservoir 600', through shaft 12b, to end effector assembly 100, similarly as described above with respect to instrument 10 (see FIG. 1). The material from reservoir 600' may be selected such that, upon injection into jaw members 110, 120, as will be detailed below, the material cools. Electrical energy may also be supplied to one or both of jaw members 110, 120 via an energy source (not shown) to heat (or cool) the material, and/or to otherwise transition the material from the fluid state to the solid state, e.g., by supplying UV energy to the material (in the case of UV-curing), depending on a particular purpose. End effector assembly 400 (FIGS. 9A-9B) shows one configuration for coupling a source of energy to the jaw members that may similarly be used in conjunction with end effector assembly 100 to supply energy to jaw members 110, 120 thereof. Instrument 10' may further include a knife assembly 180 (FIGS. 4A-4C) disposed within either of shafts 12a, 12b to permit reciprocation of a knife blade 182 (FIGS. 4A-4C) between jaw members 110, 120.

Figure 3A:
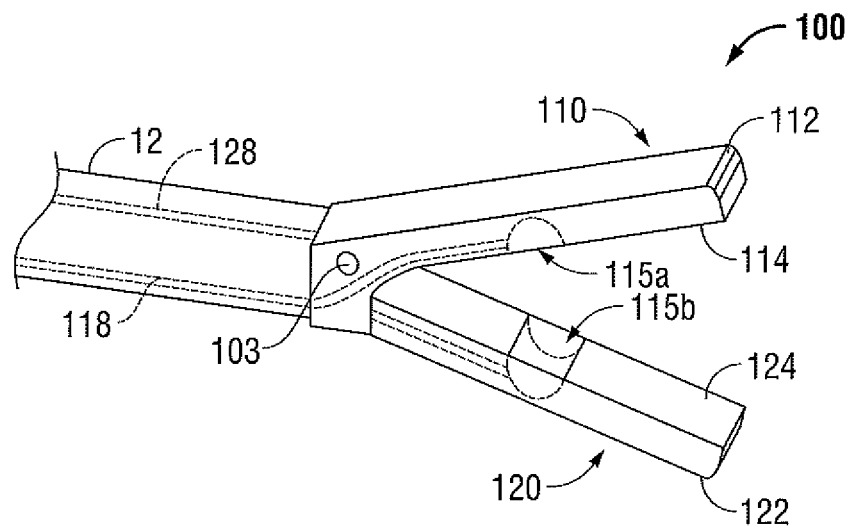
FIG. 3A is an enlarged, front, perspective view of an end effector assembly configured for use with the surgical instrument of FIG. 1 or 2 wherein jaw members of the end effector assembly are disposed in a spaced-apart position.
Figure 3B:
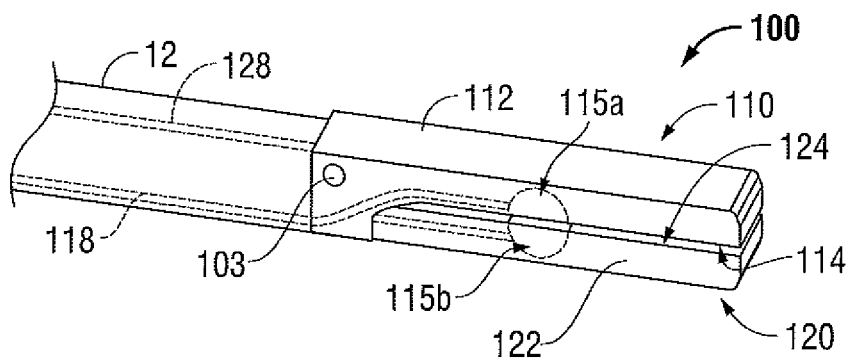
FIG. 3B is an enlarged, front, perspective view of the end effector assembly of FIG. 3A wherein the jaw members are disposed in an approximated position.

Turning now to FIGS. 3A-3B, end effector assembly 100, including jaw members 110 and 120 is configured for use with either instrument 10 or instrument 10', discussed above, or any other suitable surgical instrument. However, for purposes of simplicity and consistency, end effector assembly 100 will be described hereinbelow with reference to instrument 10 only.

As shown in FIGS. 3A-3B, jaw members 110, 120 each include an outer jaw housing 112, 122, and an opposed tissue grasping surface 114, 124, respectively. Jaw members 110, 120 each further include a cavity 115a, 115b defined within the respective tissue grasping surface 114, 124 thereof. Cavities 115a, 115b define generally hemi-cylindrical configurations such that, upon approximation of jaw members 110, 120, as shown in FIG. 3B, cavities 115a, 115b cooperate to define a cylindrical cavity 115 (FIG. 4B) extending transversely relative to the longitudinal axis "X-X." Cavities 115a, 115b are both closed-ended such that cavity 115 (FIG. 4B) is fully enclosed between jaw members 110, 120 to inhibit escape of material injected into cavity 115 (FIG. 4B). Although cavity 115 (FIG. 4B) is shown having a cylindrical configuration, other configurations of cavities 115a, 115b may also be provided, e.g., the configuration of the cavity 115 may be selected such that the complementarily-configured formed material defines a desired configuration, and/or cavity 115 (FIG. 4B) may be formed wholly in one of jaw member 110, 120 (as opposed to two cooperating cavities 115a, 115b joining to form cavity 115 (FIG. 4B)). Further, jaw members 110, 120 may be replaceable with different jaw members 110, 120 selected from a group of various different jaw members 110, 120 to achieve a desired configuration, e.g., a specific size and/or shape cavity 115 and, thus, a specific size and/or shape formed material, depending on a particular purpose. Cavities 115a, 115b are coupled to tubes 118, 128, respectively, such that, as will be described below, material from material reservoir 600 (FIG. 1) can be injected into cavities 115a, 115b via tubes 118, 128, respectively.

Figure 4A:
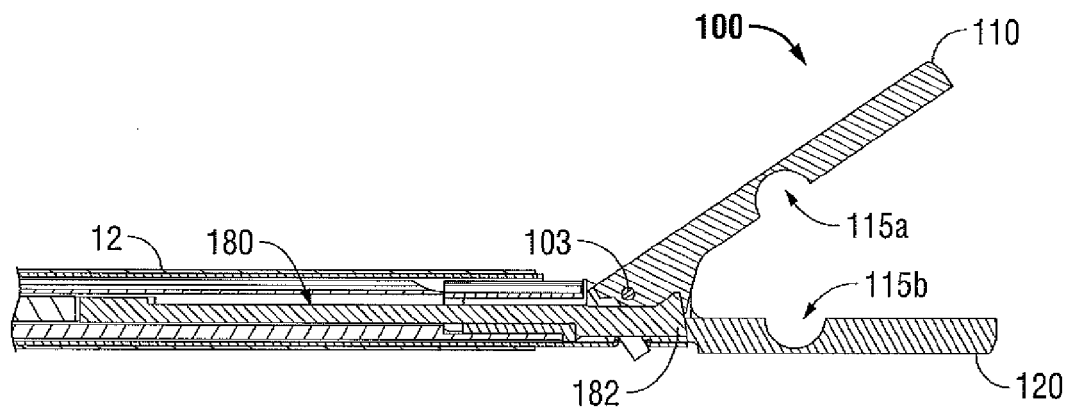
FIG. 4A is a longitudinal, cross-sectional view of another end effector assembly configured for use with the instruments of FIG. 1 or 2, wherein jaw members of the end effector assembly are disposed in a spaced-apart position.
Figure 4B:
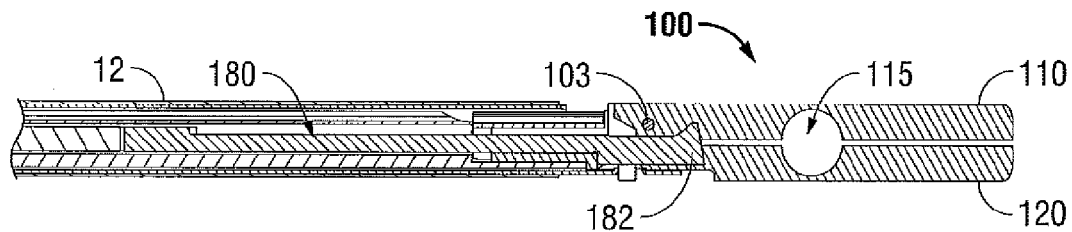
FIG. 4B is a longitudinal, cross-sectional view of the end effector assembly of FIG. 4A wherein the jaw members are disposed in an approximated position and wherein a knife blade is disposed in a retracted position.
Figure 4C:
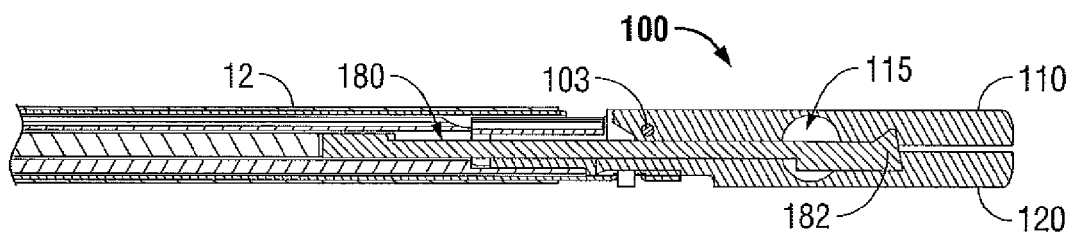
FIG. 4C is a longitudinal, cross-sectional view of the end effector assembly of FIG. 4A wherein the jaw members are disposed in the approximated position and wherein the knife blade is disposed in an extended position.

Referring now to FIGS. 4A-4C, in some embodiments, end effector assembly 100 may include a knife assembly 180. Knife blade 182 of knife assembly 180 is selectively translatable from a retracted position to an extended position, wherein knife blade 182 extends between jaw members 110, 120 to cut tissue and/or the formed material disposed therebetween. In use, initially, with jaw members 110, 120 disposed in the spaced-apart position, knife blade 182 of knife assembly 180 is disposed in a retracted position. Once jaw members 110, 120 have been moved to the approximated position, e.g., via actuation of moveable handle 40 (FIG. 1), knife blade 182 may be advanced from the retracted position (FIG. 4B) to the extended position (FIG. 4C), e.g., via activation of trigger 82 of trigger assembly 80 (FIG. 1), to divide tissue and/or the formed material disposed between jaw members 110, 120. Further, one or both of jaw members 110, 120 may include a knife channel (not explicitly shown) defined therein and configured to receive knife blade 182 therethrough to facilitate cutting of tissue and/or the formed material disposed between jaw members 110, 120.

Figure 5A:
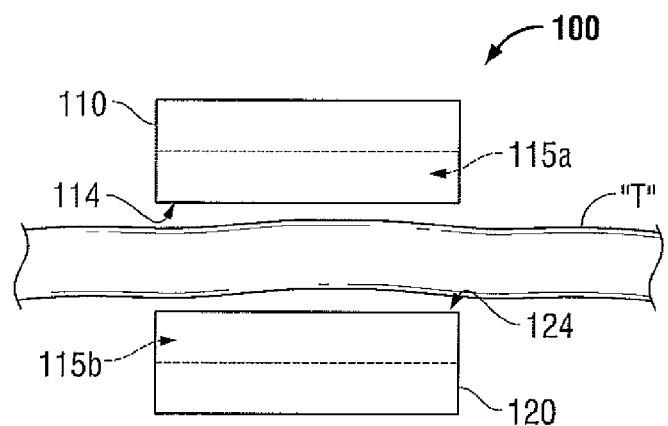
FIG. 5A is a front view of the end effector assembly of FIG. 3A shown in the spaced-apart position with tissue to be occluded disposed between the jaw members.
Figure 5B:
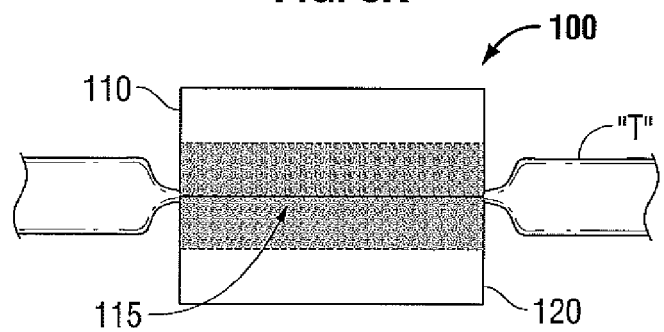
FIG. 5B is a front view of the end effector assembly of FIG. 3A shown in the approximated position grasping tissue therebetween.

With reference now to FIGS. 5A-6B, in conjunction with FIGS. 1 and 3A-4B, the use and operation of end effector assembly 100 will be described. Initially, the material, e.g., plastic, disposed within material reservoir 600 is heated, or otherwise transitioned to the fluid state, i.e., a gaseous or liquid state. With the material disposed within material reservoir 600 in a fluid state, end effector assembly 100 is positioned such that tissue "T" to be occluded is disposed between jaw members 110, 120, as shown in FIG. 5A. Thereafter, jaw members 110, 120 are moved to the approximated position, e.g., via pulling moveable handle 40 proximally relative to fixed handle 50, to grasp tissue "T" between grasping surfaces 114, 124 of jaw members 110, 120, respectively, such that tissue "T" is housed within cylindrical cavity 115 formed by the cooperating hemispherical cavities 115a, 115b defined within jaw members 110, 120, respectively.

With tissue grasped between jaw members 110, 120 and disposed within the cylindrical cavity 115, activation switch 90 may be activated to inject the heated fluid material from material reservoir 600 into cavities 115a, 115b of jaw members 110, 120, respectively, via respective tubes 118, 128 (see FIGS. 3A-3B) in an injection-molding type process. More specifically, a sufficient amount of fluid material is injected into cavities 115a, 115b such that tissue "T" housed therein is compressed and, ultimately, occluded. As can be appreciated, the specific amount of fluid material required to occlude tissue "T" depends at least in part on the size, type, and/or composition of tissue "T." In addition, as the material transitions from a heated fluid state to a solid state, the material cools and contracts around tissue "T" thereby restricting the flow of fluid, e.g., blood, therethrough.

More particularly, once tissue "T" has been sufficiently occluded via the surrounding fluid material disposed within cavity 115, activation switch 90 may be released to stop the injection of fluid material into cavity 115. Stopping the injection of the fluid material allows the fluid material surrounding tissue "T" to cool, ultimately cooling sufficiently to transition from the fluid state to the solid state (or otherwise transitioning to the solid state). Specifically, the fluid may be configured to cool from a gaseous state to the solid state (i.e., the fluid may be heated to a gaseous state and then cooled therefrom to the solid state), from a liquid state to the solid state (i.e., the fluid may be heated to a liquid state and then cooled therefrom to the solid state), or from the gaseous state to the fluid state to the solid state (i.e., the fluid may be heated to a gaseous state, allowed to cool during a first cooling to the liquid state, and then from the liquid state to the solid state during a second cooling). In the solid state, the compression on tissue "T" is maintained such that tissue "T" remains occluded.

Further, jaw members 110, 120 may be formed as heat-sinks, may include cooling elements (not shown), or may be otherwise configured to facilitate the cooling process of the fluid material from the fluid state to the solid state. For example, one or both of jaw members 110, 120 may be configured as thermoelectric, or Peltier cooling elements coupled to a source of electrical energy (not shown). In use, the electrical energy supplied to the thermoelectric, or Peltier jaw members 110, 120 creates an active heat pump for transferring heat away from the cavities 115a, 115b of respective jaw members 110, 120 (which contain the heated, fluid material disposed therein), thereby helping to cool the fluid material disposed between jaw members 110, 120 and, thus, helping to transition the material from the fluid state to the solid state.

Figure 6A:
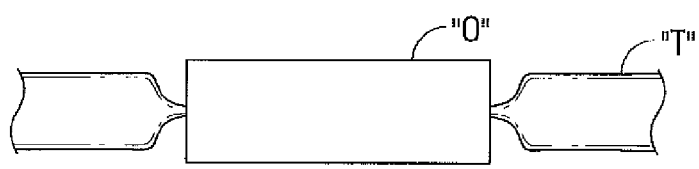
FIG. 6A is a front view of a portion of tissue that has been occluded using the end effector assembly of FIG. 3A.
Figure 6B:
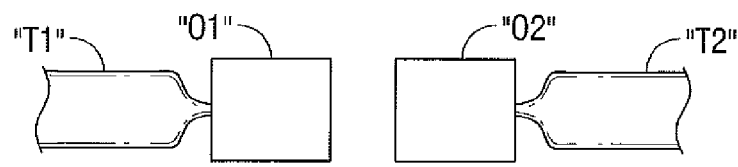
FIG. 6B is a front view of a portion of tissue that has been occluded and divided using the end effector assembly of FIG. 4A.

With the material having sufficiently cooled (or otherwise formed) such that the material is in the solid state, jaw members 110, 120 may be returned to the spaced-apart position and end effector assembly 100 may be removed from the surgical site, leaving the block of formed material (the tissue occlusion member "O") disposed about tissue "T" and maintaining tissue "T" in an occluded state, as shown in FIG. 6A. Alternatively, in embodiments where knife assembly 180 is included, prior to moving jaw members 110, 120 to the spaced-apart position and removing end effector assembly 100 from the surgical site, knife blade 182 may be advanced from the retracted position (FIG. 4B) to the extended position (FIG. 4C) to divide the newly formed tissue occlusion member "O" into first and second parts "O1" and "O2," respectively, each of which occludes a segment "T1" and "T2," respectively, of tissue "T." In either configuration, due to the biocompatibility of the injected and formed material, tissue occlusion member "O" may be left behind disposed about tissue "T" after the surgical procedure is complete to maintain a permanent occlusion of tissue "T."

Turning now to FIGS. 7A-7B, another embodiment of an end effector assembly 200 similar to end effector assembly 100 (FIGS. 3A-3B) is shown including jaw member 220. The opposed jaw member of end effector assembly 200 is substantially similar to jaw member 220 and, thus, is not shown. Further, jaw member 220 is similar to jaw member 120 (FIGS. 3A-3B), except that jaw member 220 defines a substantially U-shaped cavity 215 (FIG. 4B) therein. As such, upon injection of the fluid material through tube 218 into cavity 215 (and the corresponding cavity of the opposed jaw member (not shown)) and subsequent cooling thereof to the solid state, a U-shaped tissue occlusion member "O'" is formed. More specifically, as shown in FIG. 7B, tissue occlusion member "O'" includes a pair of legs 202, 204 interconnected via a backspan 206. Each of the legs 202, 204 occludes a portion of tissue "T" therebetween. Due to the U-shaped configuration of tissue occlusion member "O'," less of the formed material is required to be cut as knife blade 182 (FIG. 4A-4C) is advanced along cut line "C"-"C" to divide the occluded tissue "T," thus facilitating division of tissue occlusion member "O'" an tissue "T."

FIG. 8B shows another embodiment of a jaw member 320 of an end effector assembly 300 that is similar to end effector assembly 100 (FIGS. 3A-3B). The opposed jaw member of end effector assembly 300 is substantially similar to jaw member 320 and, thus, is not shown. Jaw member 320 is similar to jaw member 120 (FIGS. 3A-3B), except that jaw member 320 defines an elongated cavity 315 therein that extends at least partially along the length of jaw member 320. The opposed jaw member (not shown) of end effector assembly 300 defines a complementary configuration to that of jaw member 320. Accordingly, as shown in FIG. 8B, once the fluid material is injected into cavity 315 via tube 318 and is allowed to cool to the solid state, tissue occlusion member "O''''" is formed defining a clip-like structure that is disposed about tissue "T" to occlude tissue "T," similarly as described above with regard to end effector assembly 100 (FIGS. 3A-3B). As can be appreciated, other configurations of jaw members similar to jaw members 110 and 120, 220, or 320 may also be provided to form various different tissue occlusion members of varying configuration.

Figure 9A:
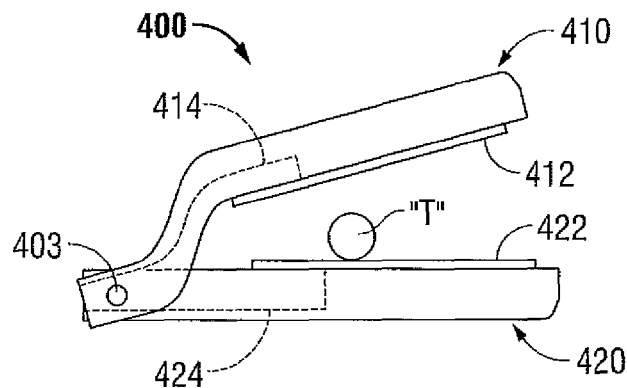
FIG. 9A is a side, cross-sectional view of an end effector assembly for coagulating tissue, wherein jaw members thereof are disposed in a spaced-apart position.
Figure 9B:
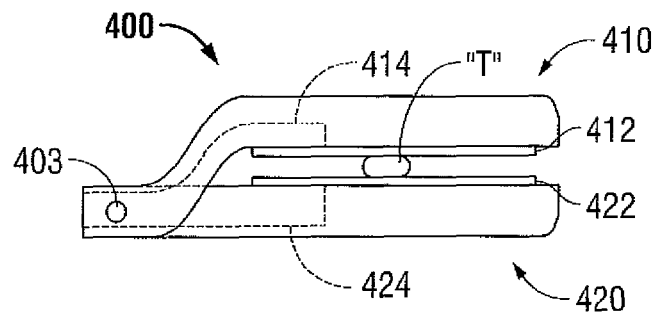
FIG. 9B is a side, cross-sectional view of the end effector assembly of FIG. 9A, wherein the jaw members are disposed in an approximated position grasping tissue therebetween.

Referring now to FIGS. 9A-9B, an end effector assembly 400 for coagulating tissue is shown. End effector assembly 400 is configured for use in conjunction with an occlusion device 500 (FIGS. 10A-10E) for coagulating and occluding tissue "T." End effector assembly 400 includes first and second jaw members 410, 420 moveable relative to one another about a pivot 403 between a spaced-apart position (FIG. 9A) and an approximated position (FIG. 9B) for grasping tissue "T" therebetween. Jaw members 410, 420 further include electrically-conductive plates 412, 422, respectively, that are coupled to a source of energy (not explicitly shown), e.g., via wires 414, 424, respectively, for conducting energy, e.g., ultraviolet (UV) energy, radiofrequency (RF) energy, or any other suitable energy, through tissue "T" to coagulate tissue "T." Once tissue "T" has been coagulated, occlusion device 500 (FIGS. 10A-10E) may be applied, as will be described below, to occlude tissue "T" and maintain tissue "T" in an occluded state. Alternatively, occlusion device 500 (FIGS. 10A-10E) may be applied to tissue "T" to occlude tissue "T" without coagulating tissue "T." Whether or not coagulation is required may depend on the size, type, and/or composition of tissue "T."

Figure 10A:
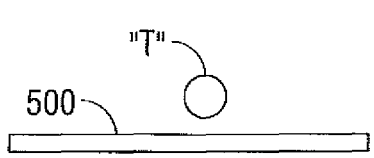
FIG. 10A a is a schematic illustration of a tissue occluding device in accordance with the present disclosure wherein the tissue occluding device is disposed in an initial position.
Figure 10B:
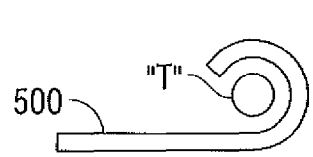
FIG. 10B is a schematic illustration of the tissue occluding device of FIG. 10A, wherein the tissue occluding device is beginning to form about tissue to be occluded.
Figure 10C:
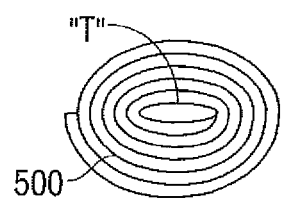
FIG. 10C is a schematic illustration of the tissue occluding device of FIG. 10A, wherein the tissue occluding device has been formed about tissue.
Figure 10D:
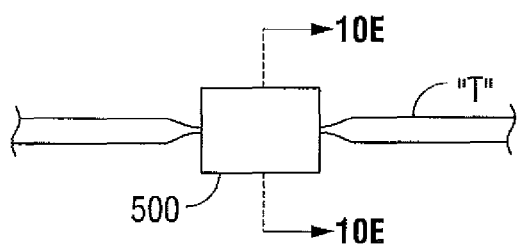
FIG. 10D is a side view of the tissue occluding device of FIG. 10A shown disposed about tissue.
Figure 10E:
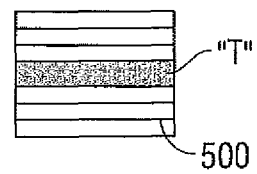
FIG. 10E is a transverse, cross-sectional view of the tissue occluding device of FIG. 10A shown disposed about tissue.

With reference to FIGS. 10A-10E, the application of tissue occlusion device 500 to tissue "T" and the particular features thereof are described. Tissue occlusion device 500 defines an elongated body, although other configurations may be provided. Initially, as shown in FIG. 10A, tissue occlusion device 500 is disposed in a substantially straight configuration. Tissue occlusion device 500 may be formed from any suitable biocompatible material, such that tissue occlusion device 500 may remain within a patient to permanently occlude tissue "T." Further, the elongated body of tissue occlusion device 500 may be a bi-stable body, e.g., a bi-stable spring, that is stable in both the substantially straight configuration (FIG. 10A) and a coiled configuration (FIGS. 10C and 10E). In other words, upon transitioning of tissue occlusion device 500 from the substantially straight configuration toward the coiled configuration, tissue occlusion device 500 wraps about tissue "T" under the spring-bias, or mechanical bias, of tissue occlusion device 500 toward the coiled configuration. Accordingly, as tissue occlusion device 500 is wrapped about tissue "T," this bias toward the coiled configuration compresses tissue occlusion device 500 about tissue "T" to occlude tissue "T."

Alternatively, or additionally, once tissue occlusion device 500 has been transitioned from the substantially straight configuration (FIG. 10A) to the coiled configuration (FIGS. 10C and 10E) to surround tissue "T," tissue occlusion device 500 may be heat-shrunk about tissue "T" via heating tissue occlusion device 500 to help ensure adequate occlusion of tissue "T." Tissue occlusion device 500 may also be shrunk, or fit about tissue "T" via application of ultraviolet (UV) energy thereto to compress tissue occlusion device 500 about tissue "T." In other words, tissue occlusion device 500 may be formed at least partially from a heat-shrink, or UV-shrink material to facilitate occlusion of tissue "T." Tissue occlusion device 500 may alternatively be formed at least partially from a shape-memory material, e.g., nitinol or another suitable shape-memory alloy, that is configured to transition from the substantially straight configuration (FIG. 10A) to the coiled configuration (FIGS. 10C and 10E) upon heating (or cooling) of tissue occlusion device 500 to a pre-determined temperature to form about tissue to occlude tissue. Further, although tissue occlusion device 500 is shown wrapped-around itself multiple times, i.e., having multiple windings, in the coiled configuration (see FIG. 10C), tissue occlusion device may alternatively be configured as a cuff or in any other suitable configuration that surrounds tissue "T" and compresses tissue "T," e.g., via heat-shrinking, UV-shrinking, or mechanical bias, to occlude tissue "T." The use and operation of the cuff-shaped tissue occlusion device, or other similarly configured tissue occlusion devices is substantially similar to that of tissue occlusion device 500, discussed below, and, thus, will not be repeated here.

Referring to FIGS. 10A-10E, the use and operation of tissue occlusion device 500 will be described. Initially, as mentioned above, tissue "T" may be coagulated, if desired, by grasping and supplying energy, e.g., RF, UV, or other energy, through tissue "T" grasped between jaw members 410, 420 of end effector assembly 400 (FIGS. 9A-9B). Next, with tissue occlusion device 500 disposed in the initial, or substantially straight configuration (FIG. 10A), tissue occlusion device 500 is positioned adjacent tissue "T" to be occluded. Thereafter, tissue occlusion device 500 is transitioned from the substantially straight configuration to the coiled configuration to compress tissue "T" by breaking, or removing tissue occlusion device 500 from the substantially straight configuration. As mentioned above, tissue occlusion device 500 may be configured as a bi-stable spring. Accordingly, tissue occlusion device 500 need only be snapped, slapped, kinked, or otherwise manipulated to break tissue occlusion device 500 from the substantially straight configuration. Once tissue occlusion device 500 has been broken, or transitioned from the substantially straight configuration, e.g., via snapping, slapping, or kinking tissue occlusion device 500, tissue occlusion device 500 begins to wrap about tissue "T," as shown in FIG. 10B, and continues under the mechanical bias to wrap about tissue "T" to the second stable state, the coiled configuration (FIG. 10C). If the mechanical bias of the coiled state of tissue occlusion device 500 is sufficient to occlude tissue "T," tissue occlusion device 500 may simply be left as is. On the other hand, if the mechanical bias is insufficient to fully occlude tissue "T," tissue occlusion device 500 may be heat-shrunk, UV-shrunk, or otherwise treated to further compress about tissue "T" to ensure adequate occlusion of tissue "T." Whether or not further compression of tissue occlusion device 500 about tissue "T" is required may depend on the size, type, and/or composition of tissue "T."

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
an end effector assembly including first and second jaw members, at least one of the jaw members moveable relative to the other between a spaced-apart position and an approximated position for grasping tissue therebetween, each jaw member defining a U-shaped cavity portion, wherein, in the approximated position of the jaw members, the U-shaped cavity portions of the jaw members cooperate to define a U-shaped cavity;
an injectable material configured for injection into the U-shaped cavity, the injectable material transitionable from a first state, facilitating injection of the injectable material into the U-shaped cavity, to a second state, wherein the injectable material is formed complementary to the U-shaped cavity to define a pair of spaced-apart, longitudinally-extending legs interconnected by a transverse backspan, the legs of the formed injectable material configured to form about and occlude tissue grasped between the jaw members; and
a knife blade selectively translatable relative to the jaw members between the legs of the formed injectable material to divide the transverse backspan of the formed injectable material and tissue extending between the legs of the formed injectable material.

2. The surgical instrument according to claim 1, further comprising a replaceable material reservoir cartridge configured to retain the injectable material therein.

3. The surgical instrument according to claim 1, wherein the injectable material is transitionable from a fluid state, facilitating injection of the injectable material into the U-shaped cavity, to a solid state, wherein the injectable material forms within the U-shaped cavity.

4. The surgical instrument according to claim 1, wherein the first state of the injectable material corresponds to a heated state and wherein the second state of the injectable material corresponds to a cooled state.

5. The surgical instrument according to claim 1, wherein the jaw members are configured to apply UV energy to the injectable material disposed within the U-shaped cavity to transition the injectable material from the first state to the second state.

* * * * *